United States Patent [19]

Shelton

[11] Patent Number: 5,527,309

[45] Date of Patent: Jun. 18, 1996

[54] PELVO-FEMORAL FIXATOR

[75] Inventor: Marvin L. Shelton, Riverdale, N.Y.

[73] Assignee: The Trustees of Columbia University in the City of New York, New York, N.Y.

[21] Appl. No.: 366,011

[22] Filed: Dec. 29, 1994

Related U.S. Application Data

[63] Continuation of Ser. No. 51,065, Apr. 21, 1993, abandoned.

[51] Int. Cl.$^6$ ................................................. A61B 17/60
[52] U.S. Cl. .............................. 606/55; 606/57; 606/59
[58] Field of Search ............................. 606/54–59, 65, 606/66, 90, 105, 130

[56]           References Cited

U.S. PATENT DOCUMENTS

| | | | |
|---|---|---|---|
| 1,997,466 | 4/1935 | Longfellow | 606/57 |
| 4,185,623 | 1/1980 | Volkov et al. | 606/56 |
| 4,361,144 | 11/1982 | Slätis et al. | 606/54 |
| 4,624,249 | 11/1986 | Alvarez Cambras | 606/54 |
| 4,768,524 | 9/1988 | Hardy | 606/54 |
| 4,784,125 | 11/1988 | Monticelli et al. | 606/56 |
| 5,127,412 | 7/1992 | Cosmetto et al. | 128/898 |
| 5,196,012 | 3/1993 | Malka | 606/54 |
| 5,213,094 | 5/1993 | Bonutti | 128/25 R |

FOREIGN PATENT DOCUMENTS

| | | | |
|---|---|---|---|
| 799741 | 1/1981 | U.S.S.R. | 606/54 |
| 1149960 | 4/1985 | U.S.S.R. | 606/54 |

OTHER PUBLICATIONS

Amicso Orthographic Catalog for Orthopedic Table (4 pages). Author unknown. Date unknown.

*Primary Examiner*—Stephen C. Pellegrino
*Assistant Examiner*—Guy V. Tucker
*Attorney, Agent, or Firm*—John P. White

[57]           ABSTRACT

The invention provides a fixator device for controlling the position of the femur relative to the pelvis during surgery, comprising a first curved rigid bar member having a pelvis anchor member disposed along its length for anchoring the bar member to the innominate bone of the pelvis, said bar member having a first end for anchoring to the upper pelvis and a second end for anchoring to the lower pelvis, and a second bar member attached at one end to the first bar member, and having a femur anchor member at its second end for anchoring to the base of the femur, to thereby control and fix the position of the femur relative to the pelvis during surgical operations.

13 Claims, 3 Drawing Sheets

PELVO-FEMORAL FIXATOR

This is a continuation of application Ser. No. 08/051,065, filed Apr. 21, 1993, now abandoned.

BACKGROUND OF THE INVENTION

The present invention relates to an external fixation device for positioning and immobilizing the femur relative to the pelvis.

A traction table has normally been used to position and immobilize the relationship between the femur and pelvis. The traction table allows application of forces to the bony skeleton indirectly through the soft tissues. Strong forces are required for long periods of time. The higher the force and longer the duration, the greater risk there is of soft tissue injury. The maximal force that can be safely generated is frequently inadequate to accomplish the desired positioning. The traction table relies on a stable pelvis and cannot be used when there is ligament and bony disruption of the pelvis. It is used is the operating room because of bulk and the need to have the patient under anesthesia.

The present invention will perform what the traction table attempted in the operating room environment in a more effective and safer fashion. In addition, because it is light weight and small, it is portable and can provide the same capability outside the operating room (i.e. in the preoperative and post-operative periods) when heavy forces need to be applied to the pelvis and femur for prolonged periods while the patient is moved about.

SUMMARY OF THE INVENTION

It is an object of the present invention to provide a means for positioning and immobilizing the leg and pelvis by direct fixation to the bony skeleton without applying pressure to the overlying soft tissues.

It is an object of the present invention to provide a means for positioning and immobilizing one hemipelvis in relation to the other hemipelvis.

It is an object of the present invention to provide a means for positioning and immobilizing the femur during the insertion of intramedullary nails in the femur.

It is an object of the present invention to provide a means for positioning and immobilizing the femur and pelvis during the performance of operative procedures on the pelvis and acetabulum.

It is an object of the present invention to provide a means for distracting the hip joint in order to facilitate arthroscopic examination and related operative procedures on the hip joint.

It is an object of the present invention to provide a means for positioning and immobilizing the pelvis and femur during the performance of total hip replacement and pelvic reconstruction.

It is an object of the present invention to provide a means for applying large distration forces to the femur with a device that is designed with a safety mechanism that prevents the application of forces known to be harmful to healthy tissues.

According to the invention, a fixator device is provided for controlling the position of the femur relative to the pelvis during surgery, comprising a first curved rigid bar member having a pelvis anchor member disposed along its length for anchoring the bar member to the innominate bone of the pelvis, said bar member having a first end with means for anchoring to the upper pelvis and a second end with means for anchoring to the lower pelvis, and a second bar member attached at one end to the first bar member, and having a femur anchor member at its second end for anchoring to the base of the femur, to thereby control and fix the position of the femur relative to the pelvis during surgical operations.

DETAILED DESCRIPTION OF THE PREFERRED EMBODIMENT

The invention provides a fixator device for controlling the position of the femur relative to the pelvis during surgery, comprising a first curved rigid bar member having a pelvis anchor member disposed along its length for anchoring the bar member to the innominate bone of the pelvis, said bar member having a first end with means for anchoring to the upper pelvis and a second end with means for anchoring to the lower pelvis; and a second bar member attached at one end to the first bar member, and having a femur anchor member at its second end for anchoring to the base of the femur, to thereby control and fix the position of the femur relative to the pelvis during surgical operations.

The second bar member may comprises means for adjusting the length of the second bar member, including a turnbuckle member having oppositely threaded sockets threadedly coupled to correspondingly threaded ends.

The means for adjusting may comprise alignment means for maintaining rotational alignment of the threaded end members. The threaded end members move toward and away from each other in response to torque applied to the turnbuckle member. A slip clutch may be used to prevent extension and retraction of the two end members when the torque applied exceeds a predetermined value. The predetermined (maximum) value of torque may be adjusted.

The second bar member may be attached to the first bar member by a first block member at the end of the first bar member said first block member having a channel for slideably receiving the second bar member, and means for releasably locking the second bar member in the channel. The means for releasably locking may comprise a threaded bore transverse to the channel and a threaded locking bolt received by said bore.

The femur anchor member may comprise a second block having at least one bore therein for receiving a threaded bolt for threading into the femur. Preferably, the femur anchor comprises two bores in said second block, and two threaded bolts.

The pelvis anchor member preferably comprises a third block having a bore for slideably receiving a threaded bolt for threading into the innominate bone, and means for releasably locking the threaded bolt within the bore. The femur anchor member is preferably connected to the second end of the second bar member by a ball and socket.

Figure 1:
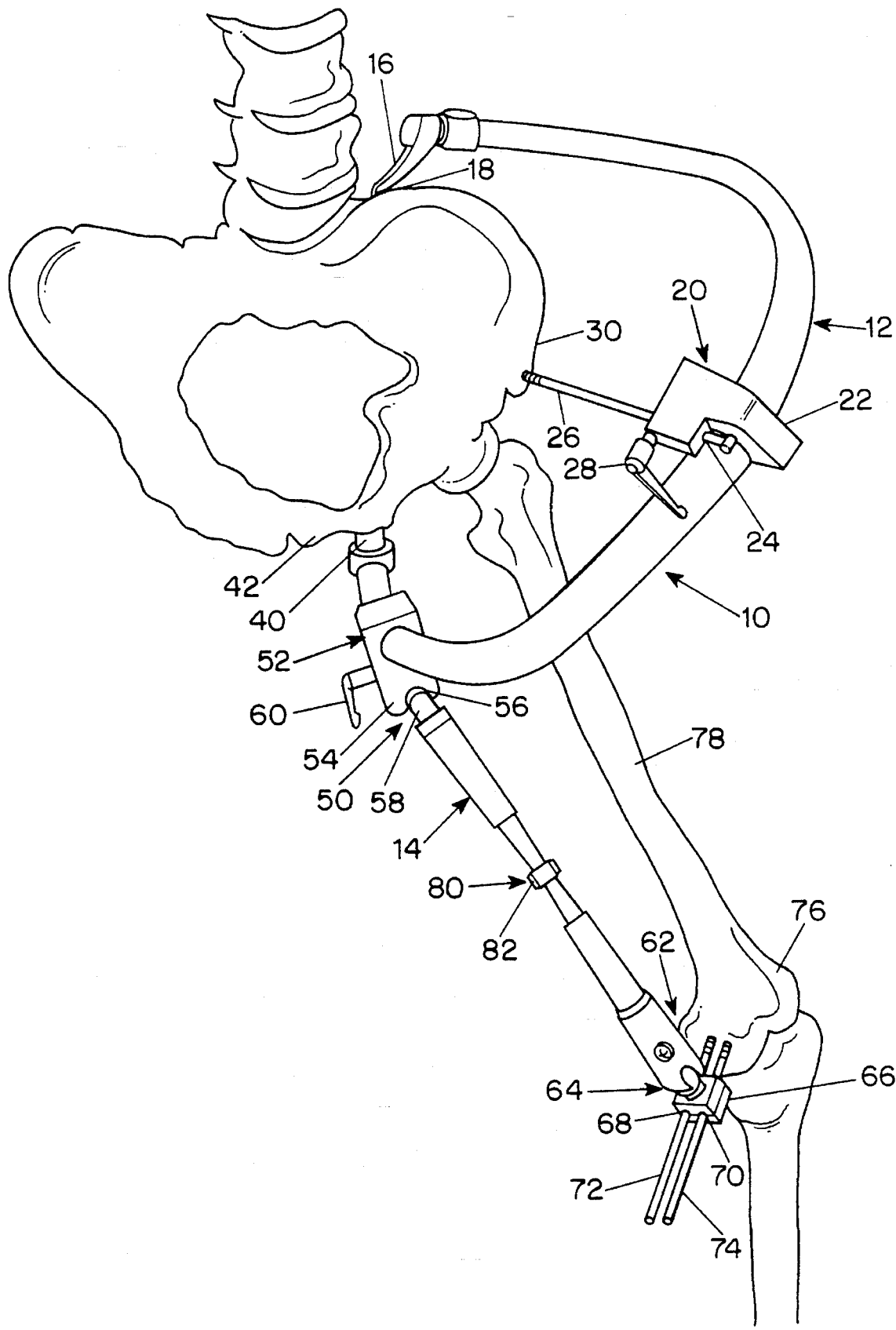
FIG. 1 is a perspective view of an embodiment of a pelvo-femoral external fixator according to the present invention, shown attached to the pelvis and femur of a skeleton.

With reference to FIG. 1, a pelvo-femoral external fixator 10 is shown having a first curved rigid bar tubular frame or pelvic half ring 12, and a second bar member or femoral extension rod 14 attached at one end of the first bar member 12. The first bar member 12 has an iliac crest fixation member 16 at one end for anchoring and attachment to the upper pelvis (ilium) 18.

The first bar member 12 has a pelvis anchor member 20 about midway along the length of the first bar member 12. The pelvis anchor member 20 comprises a block 22 mounted to the first bar member 12, a bore 24 defined in the block 22 for receiving a screw 26 and a clamp controlled by a knob 28 for releasably clamping the position of the screw 26 within the length of the bore 24. The screw has threads for anchoring into the anterior superior spine 30.

The first bar member 12 has an ischial fixation pin 40, similar to the iliac crest fixation pin 16, for anchoring and attachment to the lower, dorsal and posterior part of the pelvis (ischium) 42.

The second bar member or femoral extension rod 14 has one end 50 attached to the first bar member by a clamp 52 comprising a block 54, a bore 56 defined in the block 54 and a ball end 58 of the rod 14 received in the bore 56. The clamp 52 has a knob 60 for releasably clamping the rod ball end 58 in the clamp 52.

Disposed at the other end 62 of the rod 14 is a ball and socket arrangement 64 and block 66. The block 66 defines two parallel bores 68, 70 for receiving anchoring screws 72, 74 having threaded ends for anchoring and attachment to the distal end 76 of the femur 78.

The femoral extension rod 14 has a turnbuckle or extension section 80 comprising a rotating nut section 82 arranged so that rotation of the nut 82 in one direction causes the rod 14 to increase in length, and rotation in the other direction causes the rod 14 to decrease in length. This arrangement will be described in more detail in connection with FIG. 5.

Figure 2:
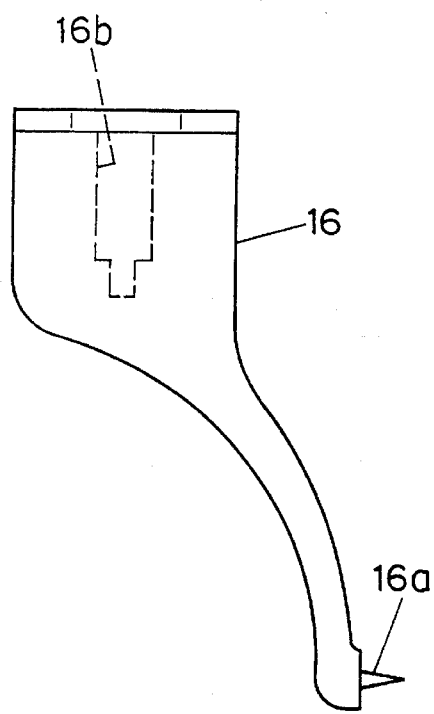
FIG. 2 is an elevational view of the iliac crest fixation member.

The iliac crest fixation member 16 is shown in more detail in FIG. 2. The member 16 has a fixation pin 16a and a bore 16b for receiving the upper end of the pelvic half ring 12.

Figure 3:
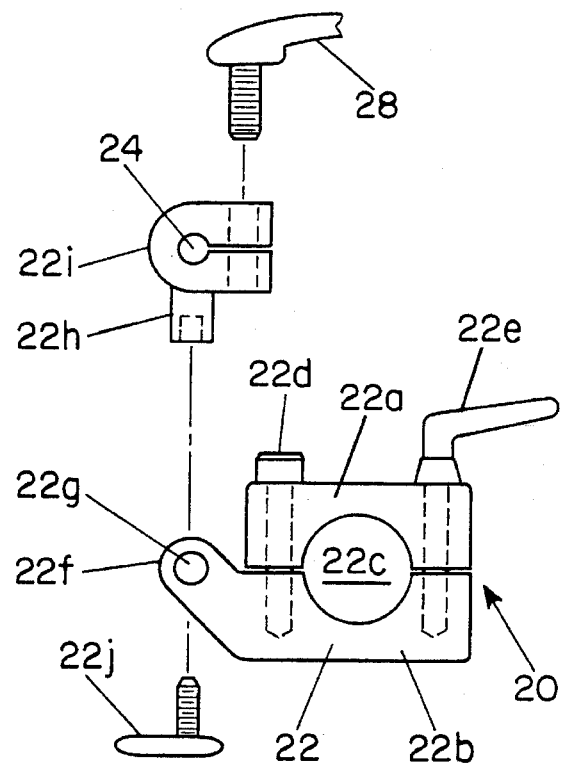
FIG. 3 is an elevational view of the pelvis anchor member.

The pelvis anchor member 20 is shown in more detail in FIG. 3. The member 20 comprises a block 22 having portions 22a and 22b each having portions 22a and 22b each having a semi-cylindrical receiving opening surface to define a cylindrical opening 22c when mated together as shown. A first screw 22d holds the portions together on one side, a clamp with knob 22e releasably clamps the portions together, allowing means to adjust the location of the pelvic half ring 12 relative thereto which is received in the cylindrical opening 22c. The block 22 includes a wing 22f having a bore 22g for receiving a shaft portion 22h of a subblock 22i. Screw 22j holds the subblock 22i relative to main block 22 in the bore 22g. The subblock 22i has a bore 24 for receiving the screw 26. A clamp with handle 28 releasably clamps the screw 26 within the bore 24. Screw 22j allows pivotal adjustment of subblock 22i relative to main block 22.

Figure 4:
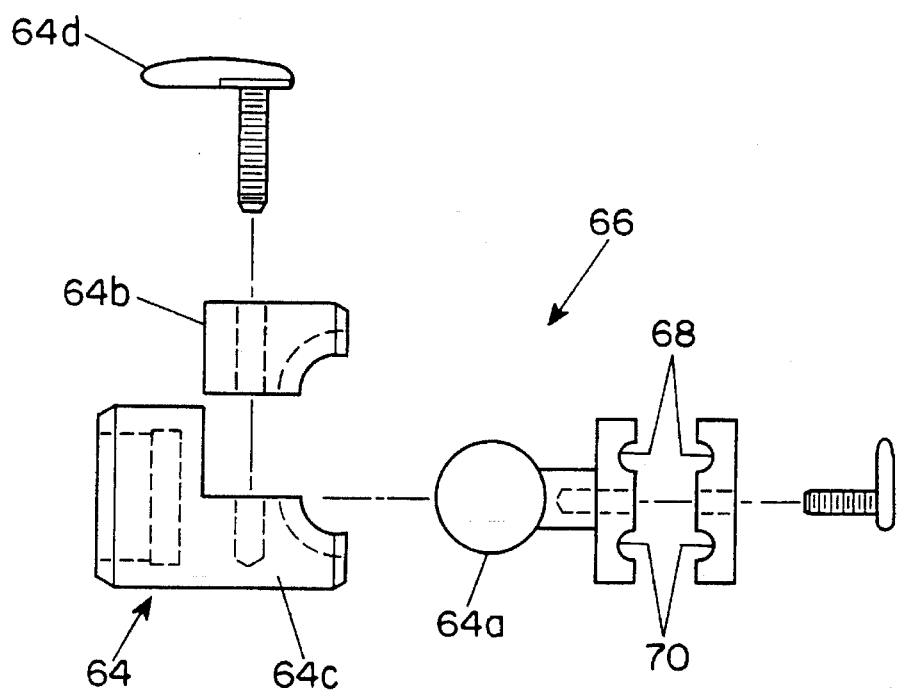
FIG. 4 is an elevational view of the block at the distal end of the second bar member or femoral extension rod.

FIG. 4 shows ball and socket arrangement of block 64 and block 66 in more detail. The ball 64a is received in a split block member having a first block member 64b and a second block member 64c, and when the proper relative positioning of ball 64a relative to the block is achieved, screw clamp 64d may be tightened.

Figure 5:
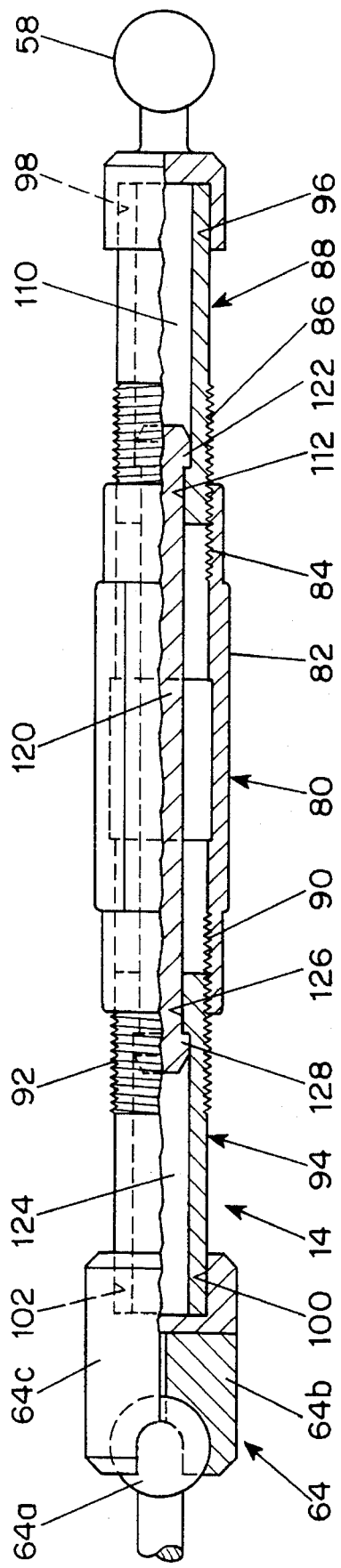
FIG. 5 is an elevational view of the central portion of the second bar member or femoral extension rod.

FIG. 5 shows the turnbuckle or extension section 80 in more detail. A particular feature of the extension section 80 is that the femoral extension rod 14 can be increased or decreased in length while also keeping the respective distal ends aligned, i.e. from rotating relative to one another. The extension section 80 comprises a rotating nut section 82 having a hex-shaped exterior cross-section. The section 82 is in the shape of a tube having a hollow center. The right end of the section 82 has a right-hand internal thread at 84 and threadingly mates with and receives a right-hand externally threaded end 86 of a right extension piece 88. Similarly, the left end of section 82 has a left-hand internal thread at 90 and threadingly mates with and receives a left-hand externally threaded end 92 of a left extension piece 94. The right end 96 of right extension piece 88 is fixed inside socket 98 of the right ball joint member having ball end 58. The left end 100 is likewise fixed inside socket 102 of block 64.

The right extension piece 88 has a hollow center region 110 of rectangular or other non-circular cross-section. This region 110 continues to the left in a slightly smaller cross-section region defined by wall 112.

This region 110 slidingly receives the right end of an alignment member 120 having an enlarged right end portion 122, whose cross-section matches the cross-section of region 110. The left extension piece 94 similarly has a hollow region 120 of rectangular or other non-circular cross-section, which region 124 continues to the right in a slightly smaller cross-section region defined by wall 126. The region 124 slidingly receives the left end of the alignment member 120 having an enlarged left end portion 128, whose cross-section matches the cross-section of region 124.

The arrangement just described of alignment member 120, along with the cross-sectional configuration of regions 110 and 124 allow the right extension piece 88 and left extension piece 94 to move axially toward and away from each other to shorten or lengthen the overall length of femoral extension rod 14, but also keeps the right extension piece 88 and left extension piece 94 in rotational alignment. This advantageously keeps the ends 64 and 58 from rotating relative to one another. Also, the enlarged end portions 122, 128 of the alignment member 120 provide the maximum longitudinal extent of the rod 14, and keep the right piece 88 and left piece 94 from coming off.

Figure 6:
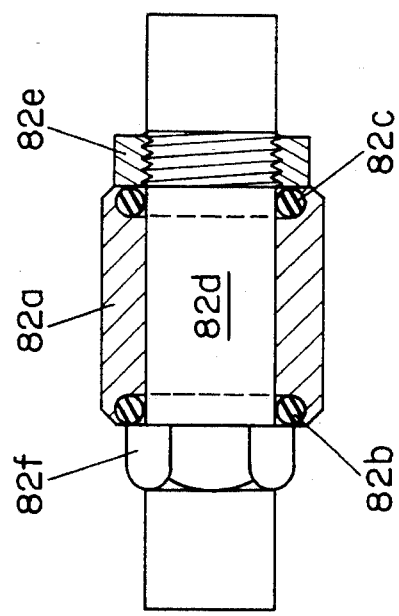
FIG. 6 is an elevational view of a torque control and adjustment device for the femoral extension rod of FIG. 5.

The extension section 80 may have a slip clutch arrangement which allows the rod 14 to be extended and/or shortened only when the torque on the rotating nut section is less than a predetermined maximum torque. This may be accomplished by providing the arrangement of FIG. 6, for example. Here the rotating nut 82 is similar to the one just described and shown with reference to FIG. 5, but comprises several pieces, including an outer piece 82a having a hex-shaped exterior cross-section, two rings 82b, c of torque-transmitting resilient material made of rubber, for example, and an inner member 82d. The torque value at which slippage occurs may adjusted by rotating torque control device 82e relative to fixed hex member 82f, which will either compress or relax torque-transmitting material 82b, c, which will increase or decrease the point at which this material will slip and not transmit torque. The torque control device is internally threaded onto threads of member 82d. Other arrangements for controlling torque will readily occur to those skilled in the art.

The fixation pins 16 and 40 are preferably made of biologically compatible stainless steel. The clamps and first and second members are preferably made of titanium. The knobs of the clamps are preferably made of heat resistant plastic.

An operative procedure employing the pelvo-femoral external fixator will now be described as one exemplary way of using the fixator according to the invention.

The patient is placed supine on an operating table that is suitable for use with an image intensifier. Anesthesia is administered. A wedge or sandbag is placed under the pelvis on the side to be operated upon. The injured leg is abducted and held by securing the foot to an IV pole. Hair is removed from the perineum, buttocks, lower back, lower abdomen, thigh and knee as far as mid-calf on the affected side. The anus and genitalia are covered with adhesive steridrape. The skin is thoroughly prepped in the usual orthopaedic manner and sterile drapes are applied that allow positioning and manipulation of the affected leg and access to the sites of placement of the skeletal fixation points on the pelvis and femur. A leg holder that can be sterilized and placed in the operative field is useful to support the calf during placement of the pelvo-femoral distrator.

A suitably sized pelvic half ring 12 is selected from a variety of differently sized pelvic half rings. In this way, a group of differently sized rings may be provided in a package, to cover a wide variety of patients having differently sized pelvic areas. The sizes of the rings may be determined statistically or empirically and are intended to cover the universe of potential patients. An iliac crest fixation pin is selected from a group of differently sized pins in the same manner. The horizontal crest just adjacent to the posterior iliac spine is palpated and a 1 cm skin incision is made over the site. An awl is introduced through the subcutaneous tissue and the raphe between the abdominal muscles and the abductors is identified. The periosteum in the center of the superior surface of the crest is identified and indented with the tip of the awl.

The ischial tuberosity is identified by palpation and a 1 cm incision is made over the flat surface that is not covered by muscle and is close to the skin. The awl is used to locate the center of the surface and indent the periosteum and cortex. A 2 mm K wire is inserted 2 cm into the ischium.

The anterior superior iliac spine is palpated and a 1 cm skin incision is made over it. The awl is used to penetrate the periosteum and dent the cortex.

The skeletal pins are attached to the fixator frame. The frame is positioned. The tip of the iliac pin is put into the previously dented bone. Next, the ischial pin is screwed into the bone. The shoulder on the pin engages the cortex of the ischium which forces the iliac pin to penetrate the iliac cortex. When the frame feels stable except for rotation, the third antirotary pin is inserted through the clamp on the pelvic half ring into the anterior superior spine to a depth of about 1 cm. This completes the attachment of the pelvic portion of the fixator.

Through stab wounds and using the awl as previously described, two fixation pins are then placed into the distal femur in the epiphyseal bone from the medial side (but nearly penetrating the lateral cortex) and attached to the femoral pin clamp. Pin placement is checked in two planes using the C-arm.

Longitudinal traction is applied on the leg in line with the extremity. The femoral extension rod is attached to the femoral pin block and to a clamp on the pelvic frame.

Guided by the image intensifier, the distal fragment and leg are manipulated to align the fracture. The extension rod is then used to overcome over-riding of the femoral fracture. If the proximal and distal fragments are in the periosteal/ muscle tube, reduction is easily accomplished. If the proximal fragment has buttoned holed through the periosteal and muscle sleeves, one should first try to overcome this by placing an intramedullary rod in the proximal fragment for direct control of the fragment. If this maneuver fails to achieve reduction of the fracture, one should perform an open reduction through a short lateral incision over the lateral intramuscular septum.

A guide wire is then passed across the fracture site. Reaming of the intramedullary canal is performed. A suitable intramedullary nail is inserted. Interlocking distally and proximally is carried out.

According to the foregoing, a preferred embodiment and one exemplary operative procedure for using the embodiment has been shown and described. However, numerous variations and modifications will occur to those skilled in the art. Thus, the present invention is not limited to the preferred embodiment, and its scope is defined by way of the appended claims.

What is claimed:

1. A fixator device for controlling the position of the femur relative to the pelvis during surgery, comprising:

a first curved rigid bar member having a pelvis anchor member disposed along its length for anchoring the bar member to a single innominate bone of the pelvis, said bar member having a first end with means for anchoring to the upper half of the single innominate bone and a second end with means for anchoring to the lower half of the single innominate bone; and a second bar member attached to the second end of the first bar member at one end of the second bar member, and having a femur anchor member at its second end for anchoring to the base of the femur, to thereby control and fix the position of the femur relative to the pelvis during surgical operations.

2. The fixator device according to claim 1, wherein the second bar member comprises means for adjusting the length of the second bar member.

3. The fixator device according to claim 2, wherein the means for adjusting comprises a turnbuckle member having oppositely threaded sockets threadedly coupled to correspondingly threaded end members.

4. The fixator device according to claim 3, wherein the means for adjusting comprises alignment means for maintaining rotational alignment of the threaded end members.

5. The fixator device according to claim 3, wherein the means for adjusting comprises moving the threaded end members toward and away from each other in response to torque applied to the turnbuckle member.

6. The fixator device according to claim 3, wherein the means for adjusting comprises slip clutch means which prevents movement of the threaded end members toward and away from each other when the torque applied to the turnbuckle member exceeds a predetermined value.

7. The fixator device according to claim 6, further comprising means for adjusting the predetermined value of torque.

8. The fixator device according to claim 1, wherein the second bar member is attached to the first bar member by a first block member at the end of the first bar member, said first block member having a channel for slideably receiving the second bar member, and means for releasably locking the second bar member in the channel.

9. The fixator device according to claim 8, wherein the means for releasably locking comprises a threaded bore transverse to the channel and a threaded locking bolt received by said bore.

10. The fixator device according to claim 1, wherein the femur anchor member comprises a femur bolt block having at least one bore therein for receiving a threaded bolt for threading into the femur.

11. The fixator device according to claim 10, wherein the femur anchor comprises two bores in said femur bolt block, and two threaded bolts.

12. The fixator device according to claim 1, wherein the pelvis anchor member comprises a pelvis bolt block having a bore for slideably receiving a threaded bolt for threading into the single innominate bone, and means for releasably locking the threaded bolt within the bore.

13. The fixator device according to claim 1, wherein the femur anchor member is connected to the second end of the second bar member by a ball and socket.

* * * * *